ns* ## United States Patent [19]

Bambury et al.

[11] 4,008,221
[45] Feb. 15, 1977

[54] 6-[(2,4-DIOXO-1-PYRIMIDINYL-)ACYLAMINO]PENICILLIN DERIVATIVES

[75] Inventors: Ronald E. Bambury; Michael L. Edwards, both of Cincinnati; Laird F. Miller, Loveland, all of Ohio

[73] Assignee: Richardson-Merrell Inc., Wilton, Conn.

[22] Filed: Feb. 9, 1976

[21] Appl. No.: 656,653

Related U.S. Application Data

[62] Division of Ser. No. 413,564, Nov. 7, 1973, Pat. No. 3,956,288.

[52] U.S. Cl. .................................... 260/239.1
[51] Int. Cl.² ...................................... C07D 499/48

[58] Field of Search .................................. 260/239.1

[56] References Cited

UNITED STATES PATENTS 3,757,013  9/1973  Bickel et al. .................. 260/243 C

*Primary Examiner*—Gerald A. Schwartz
*Attorney, Agent, or Firm*—William J. Stein; Eugene O. Retter; George W. Rauchfuss, Jr.

[57] ABSTRACT

Novel [substituted(2,4-dioxo-1-pyrimidinyl-)acetylamino]penicillin and cephalosporin derivatives are prepared which are useful antibacterial agents.

4 Claims, No Drawings

6-[(2,4-DIOXO-1-PYRIMIDINYL)ACYLAMINO]-PENICILLIN DERIVATIVES

This is a division of application Ser. No. 413,564, filed No. 7, 1973 now U.S. Pat. No. 3956,288.

FIELD OF THE INVENTION

This invention relates to novel derivatives of [substituted (2,4-dioxo-1-pyrimidinyl)acetylamino]penicillins and cephalosporins, to their methods of preparation, and to their usefulness as antibacterial agents.

BACKGROUND OF THE INVENTION

This invention relates to new synthetic compounds of the penicillin and cephalospor in classes which are useful as antibacterial agents. These compounds possess a high degree of activity against a large number of microorganisms, particularly penicillinase-producing micro-organisms. As antibacterial agents the compounds of this invention are therapeutically effective in the treatment of infectious diseases due to gram-positive and gram-negative bacteria in poultry and animals, including man. In addition, the compounds of this invention are useful as animal feed supplements and as the active ingredient in germicidal preparations employed as surface disinfectants.

Prior Art

The cleavage of penicillins to 6-aminopenicillanic acid in 1959 and the chemical cleavage of cephalosporin to give the corresponding 7-aminocephalosporanic acid made possible the synthesis of new synthetic penicillins and cephalosporins not previously available via fermentation procedures. Acylation of the amino group has produced derivatives containing a heterocyclic ring in the 6-position side chain, as in the case of the penicillin series, or in the corresponding 7-position side chain, as in the case of the cephalosporin series. Such heterocycles include the thiophene ring, as for example, U.S. Pat. Nos. 3,218,318, 3,449,338 and 3,498,979 (cephaloridine and cephalothin); pyridine, U.S. Pat. No. 3,422,100 (cephapirin); picoline, U.S. Pat. No. 3,553,203; hydantoin, U.S. Pat. No. 3,227,712; and various other nitrogen containing heterocycles including pyrrolidine and nicotinic acid, U.S. Pat. No. 3,308,120.

In each instance the heterocyclic moiety is attached to a side chain, generally that of an acetyl radical, via one of the ring carbon atoms. The present invention is concerned with 2,4-dioxo-1-pyrimidinyl derivatives which are linked directly to the acetyl radical through the hetero atoms. Examples known to the inventors containing this type of linkage, and in this regard representing the closest prior art, are the tetrazole ring in U.S. Pat. No. 3,516,997 (cefazolin) and certain quinazolinyl derivatives of penicillanic acis, U.S. Pat. No. 3,652,547.

SUMMARY OF THE INVENTION

This invention relates to novel 2,4-dioxo-1-pyrimidinyl penicillin and cephalosporin derivatives. More particularly, this invention relates to [substituted (2,4diox-o-1-pyrimidinyl)acetylamino]penicillin and cephalosporin derivatives which are useful as antibacterial agents and which may be represented by the general formula:

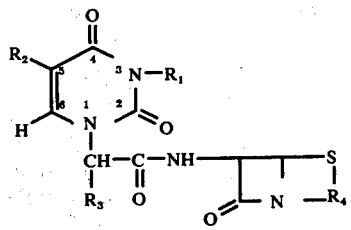

wherein
$R_1$ is hydrogen and methyl;

$R_2$ is selected from the group consisting of hydrogen, halogen, hydroxyl, lower alkyl, trifluoromethyl, nitro, amino, acetyl, cyano, carboxy, carbomethoxy and carbethoxy;

$R_3$ is selected from the group consisting of hydrogen, methyl, phenyl, carboxy, carbomethoxy and carbethoxy;

$R_4$ is selected from the group consisting of

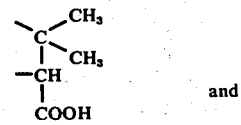 and 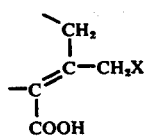

wherein X is hydrogen, hydroxy, acetoxy, N-pyridinium, 5-methyl-1,3,4-thiadiazol-2-ylthio and 1-methyl-1,2,3,4-tetrazol-5-ylthio; and
the pharmaceutically acceptable salts thereof.

The compounds of the present invention are prepared by the condensation of a 6-aminopenicillanic acid or a 7-aminocephalosporanic acid with a (substituted)2,4-dioxo-1-pyrimidinylacetic acid as illustrated in the following reaction scheme.

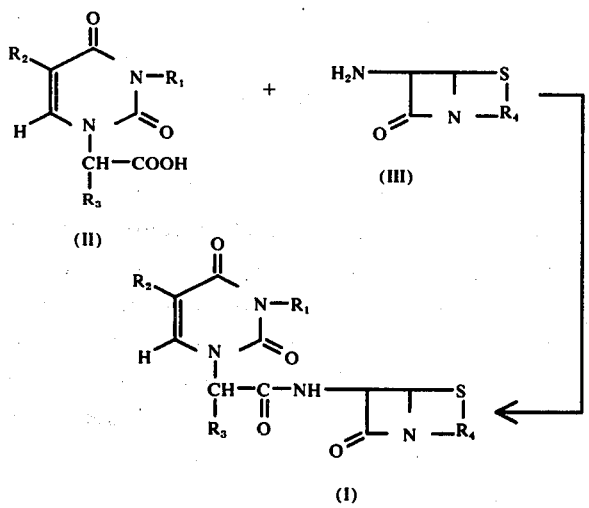

DETAILED DESCRIPTION OF THE INVENTION

All of the compounds of the present invention contain a 2,4-dioxo-1-pyrimidinyl radical or a 2,4-pyrimidinedione moiety at the terminal position of the acetylamino side chain, as indicated in general Formula (I) above. In the case of the penicillin series, the acetylamino side chain is enumerated as the 6-position, whereas in the cephalosporin series of compounds the 7-position is enumerated. The numbering system for these two series of compounds is illustrated for the intermediates 6-aminopenicillanic acid (IV) and 7-aminocephalosporanic acid (V) below:

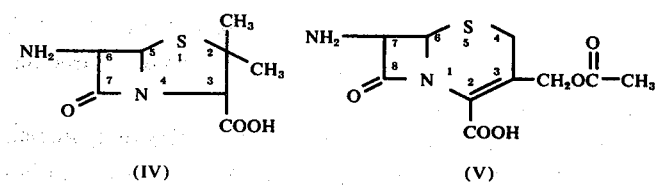

The 2,4-pyrimidinedione moiety attached to the acetylamino side chain can be either substituted or unsubstituted. The various substituents are located either on the 5-position or the 3-position of the 2,4-dioxo-pyrimidine nucleus. The substituents at the 5-position, represented by the symbol $R_2$, include the following radicals: halogen, hydroxyl, lower alkyl, trifluoromethyl, nitro, amino, cyano, carboxyl and the methyl and ethyl esters of the carboxyl radical. The term halogen includes the fluoro, chloro, bromo and iodo radicals. The term lower alkyl as used herein includes both straight and branched chain aliphatic hydrocarbon radicals having from 1 to 4 carbon atoms. Specifically included are such members as methyl, ethyl, propyl, isopropyl, butyl, isobutyl, and the t-butyl radicals. Substitution at the imide nitrogen atom located at the 3-position of the pyrimidine ring is much more limited in scope and includes hydrogen or a methyl radical, as indicated by the symbol $R_1$.

As to the acetylamino or acetamido portion of the molecule, substitution of the 2-methyl group is, of course, mandatory with the 2,4-dioxo-1pyrimidinyl radical. Additionally, the 2-methyl group may contain substitution in the form of a methyl radical, a phenyl radical or a carboxyl radical as represented by the symbol $R_3$. When $R_3$ is a methyl radical, for example, the compounds are more properly termed as propionylamino derivatives of 6aminopenicillanic acid or of 7-amino-cephalosporanic acid. For the sake of simplicity and uniformity in nomenclature, however, these derivatives will be termed as 2-(substituted) acetylamino derivatives. Thus, for example, in the case of a cephalosporanic acid derivative in which $R_3$ is methyl and the 2,4-pyrimidinedione remains unsubstituted, the compound is designated as 7-[2-(2,4-dioxo-1-pyrimidinyl)2-methylacetylamino]cephalosporanic acid. Similarly, where $R_3$ represents the phenyl radical, the same compound is designated as 7-[2-(2,4-dioxo-1-pyrimidinyl)-2-phenylacetylamino]cephalosporanic acid. In addition to the carboxyl radical at $R_3$ the methyl and ethyl esters or the carbomethoxy and carbethoxy radicals are contemplated to be within the scope of the present invention.

This invention is essentially concerned with the preparation and description of 2-(2,4-dioxo-1-pyrimidinyl)-acetylamino derivatives of β-lactam antibiotics. These derivatives are prepared by condensation with the readily available 6-amino penicillanic acid or any of the available 7-aminocephalosporin intermediates. Thus, where $R_4$ is the radical

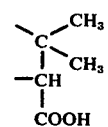

derivatives of the penicillin series are delineated, whereas when $R_4$ is the radical

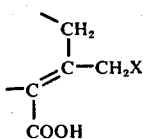

derivatives of the cephalosporin series are described.

Variations within the cephalosporin series are further indicated by the symbol X. Thus, where X is hydrogen the desacetoxycephalosporanic acids are delineated; and where the symbol X is hydroxyl, the desacetylcephalosporanic acids are indicated. Where the symbol X represents an acetoxy radical the β-lactam nucleus is that of cephalosporanic acid. Additional substituents at the 3-position of decephalosporanic acid which are included within the purview of the present invention and represented by the symbol X are the 3-pyridiniummethyl, the 3-(5-methyl-1,3,4-thiadiazol-2-ylthio)-methyl and the 3-(1-methyl-1,2,3,4-tetrazol-5-ylthio)-methyl radicals.

The pharmaceutically acceptable salts of the compounds of Formula (I) above include the non-toxic, carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and additional amines which have been used to form non-toxic salts with benzylpenicillin. These salts can be prepared using conventional means such as contacting and neutralizing a solution of the carboxylic acid in a polar solvent with a stoichiometric quantity of base.

Illustrative specific base compounds which are encompassed by Formula (I) above include: 6-[2-(2,4-dioxo-1-pyrimidinyl)acetylamino[penicillanic acid, 6-[2-(2,4-dioxo-5-ethyl-1-pyrimidinyl)acetylamino]-penicillanic acid, 6-[2-(5-acetyl-2,4-dioxo-1-pyrimidinyl)-2-phenylacetyl-amino]penicillanic acid, 6-[2-(2,4-dioxo-5-hydroxy-3-methyl-1-pyrimidinyl)acetylamino]penicillanic acid, 6-[2-(2,4-dioxo-5-trifluoromethyl-1-pyrimidinyl)acetylamino]penicillanic acid, 6-[2-(5-carboxy-2,4-dioxo-3-methyl-1-pyrimidinyl)-2-carboxyacetylamino]penicillanic acid, 7-[2-(2,4-dioxo-1-pyrimidinyl)acetylamino]cephalosporanic acid, 7-[2-(2,4-dioxo-5-nitro-1-pyrimidinyl)-acetylamino]cephalosporanic acid, 7-[2-(5-carbethoxy-2,4-dioxo-3-methyl-1-pyrimidinyl)-2-carbethoxyacetylamino]-cephalosporanic acid, 7-[2-(5-acetyl-2,4-dioxo-1-pyrimidinyl)acetylamino]cephalosporanic acid, 7-[2-(5-bromo-2,4-dioxo-3-methyl-1-pyrimidinyl)-2-methylacetylamino]-cephalosporanic acid, 7-[2-(5-cyano-2,4-dioxo-1-pyrimidinyl)acetylamino]cephalosporanic acid, 7-[-(2,4-dioxo-1-pyrimidinyl)acetylamino]desacetoxycephalosporanic acid, 7-[2-(5-amino-2,4-dioxo-3-methyl-1-pyrimidinyl)acetylamino]-desacetoxycephalosporanic acid, 7-[2-(2,4-dioxo-5-fluoro-1-pyrimidinyl)-2-phenylacetylamino]desacetoxycephalosporanic acid, 7-[2-(5-carbomethoxy-2,4-dioxo-3-methyl-1-pyrimidinyl)-2-carbomethoxyacetylamino]desacetoxycephalosporanic acid, 7-[2-(5-cyano-2,4-dioxo-1-pyrimidinyl)-acetylamino]desacetoxycephalosporanic acid, 7-[2-(2,4-dioxo-3-methyl-1-pyrimidinyl)-2-methylacetylamino]-desacetoxycephalosporanic acid, 7-[2-(2,4-dioxo-1-pyrimidinyl)acetylamino]desacetylcephalosporanic acid, 7-[2-(2,4-dioxo-5-nitro-1-pyrimidinyl)-2-phenylacetylamino]-desacetylcephalosporanic acid, 7-[2-(2,4-dioxo-3-methyl-5-trifluoromethyl-1-pyrimidinyl)acetylamino]desacetylcephalosporanic acid, 7-[2-(2,4-dioxo-5-iodo-1-pyrimidinyl)-2-methylacetylamino]desacetylcephalosporanic acid, 7-[2-(2,4-dioxo-3-methyl-5-propyl-1-pyrimidinyl)acetylamino]-desacetylcephalosporanic acid, 7-[2-(5-carbethoxy-2,4-dioxo-1-pyrimidinyl)-2-carbethoxyacetylamino]desacetyl-cephalosporanic acid, 7-[2-(2,4-dioxo-1-pyrimidinyl)-acetylamino]-3-(pyridiniummethyl)decephalosporanic acid, 7-[2-(5-chloro-2,4-dioxo-3-methyl-1-pyrimidinyl)-2-methyl-acetylamino]-3-(pyridiniummethyl)decephalosporanic acid, 7-[2-(2,4-dioxo-5-ethyl-1-pyrimidinyl)acetylamino]-3-(pyridiniummethyl)decephalosporanic acid, 7-[2-(5-acetyl-2,4-dioxo-1-pyrimidinyl)-2-phenylacetylamino]-3-(pyridiniummethyl)decephalosporanic acid, 7-[2-(5-carboxy-2-2,4-dioxo-1-pyrimidinyl)-2-carboxyacetylamino]-3-(pyridinium-methyl)decephalosporanic acid, 7-[1-(5-amino-2,4-dioxo3-methyl-1-pyrimidinyl)acetylamino]-3-(pyridiniummethyl)-decephalosporanic acid, 7-[2-(2,4-dioxo-1-pyrimidinyl)-methyl]decephalosporanic acid, 7-[2-(5-butyl-2,4-dioxo-1-pyrimidinyl)-2-phenylacetylamino]-3-[(5-methyl-1,3,4-thiadiazol-2-ylthio)methyl]decephalosporanic acid, 7-[2-(2,4-dioxo-5-iodo-3-methyl-1-pyrimidinyl)acetylamino]-3-[(5-methyl-1,3,4-thiadiazol-2-ylthio)methyl]decephalosporanic acid, 7-[2-(2,4-dioxo-5-hydroxy-1-pyrimidinyl)-2-methylacetylamino]-3-[(5-methyl-1,3,4-thiadiazol-2-ylthio)methyl]decephalosporanic acid, 7-[2-(5-carbomethoxy- 2,4-dioxo-1-pyrimidinyl)-2-carbomethoxyacetylamino]-3-[(5-methyl-1,3,4-thiadiazol-2-ylthio)methyl]decephalosporanic acid, 7-[2-(2,4-dioxo-3-methyl-5-nitro-1-pyrimidinyl-)acetylamino]-3-[(5-methyl-1,3,4-thiadiazol-2-ylthio)-methyl]decephalosporanic acid, 7-[2-(2,4-dioxo-1-pyrimidinyl)acetylamino]-3-[(1-methyl-1,2,3,4-tetrazol-5-ylthio)-methyl]decephalosporanic acid, 7-[2-(2,4-dioxo-5-trifluoromethyl-1-pyrimidinyl)-2-methylacetylamino]-3-[(1-methyl-1,2,3,4-tetrazol-5-ylthio)methyl]decephalosporanic acid, 7-[2-(5-acetyl-2,4-dioxo-1-pyrimidinyl)acetylamino]-3-[(1-methyl-1,2,3,4-tetrazol -5-ylthio)methyl]decephalosporanic acid, 7-[2-(2,4-dioxo-3-methyl-5-nitro-1-pyrimidinyl)acetylamino]-3-[(1-methyl-1,2,3,4-terrazol-5-ylthio)-methyl]decephalosporanic acid, 7-[2-(5-amino-2,4-dioxo-3-methyl-1-pyrimidinyl)acetylamino]-3-[(1-methyl-1,2,3,4-tetrazol-5-ylthio)methyl]decephalosporanic acid and 7-[2-(5-carboxy-2,4-dioxo-1-pyrimidinyl)-2-carboxyacetylamino]-3-[(1-methyl-1,2,3,4-tetrazol-5-ylthio)methyl]-decephalosporanic acid.

The products of the present invention are prepared by reacting a 6-aminopenicillanic acid or 7-aminocephalosporanic acid, or derivative thereof, having the formula

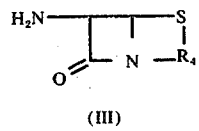

(III)

with a 2,4-dioxo-1-pyrimidinyl-(substituted)-acetic acid having the formula

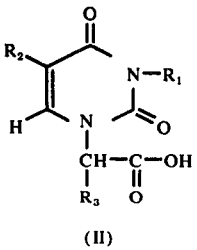

(II)

wherein the symbols $R_1$, $R_2$ and $R_3$ have the values previously assigned.

The β-lactam starting materials (III) are all known compounds. The compound, 6-aminopenicillanic acid, having the formula

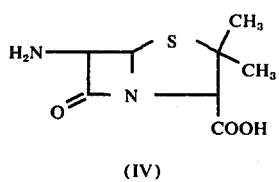

(IV)

can be prepared using biological methods and can also be prepared by the hydrolysis of various penicillins as described in U.S. Pat. No. 3,499,909.

Hydrolysis of the antibiotic cephalosporin C results in the formation of 7-aminocephalosporanic acid, Loder et al., Biochem. J. 79, 408–416 (1961) having the formula

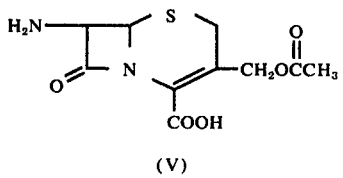

(V)

The compound 7-aminodesacetoxycephalosporanic acid having the formula

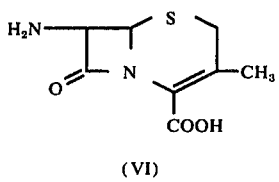

(VI)

is prepared by the catalytic reduction of cephalosporin C, followed by the hydrolytic removal of the 5-aminoadipoyl side chain as described in U.S. Pat. No. 3,129,224.

Treatment of cephalosporin C with an acetyl esterase prepared from orange peel, Jeffery et al., Biochem. J., 81, 591 (1961) results in the formation of 3-hydroxymethyl-7-aminodecephalosporanic acid, (7-aminodesacetylcephalosporanic acid), having the formula

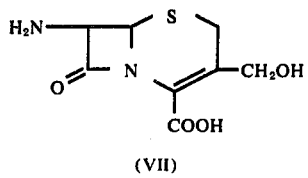

(VII)

Treatment of cephalosporin C with pyridine followed by an acid hydrolysis produces the compound, 7-amino-3-(pyridiniummethyl)decephalosporanic acid having the formula shown below. The preparation of this compound is known in the art and described, for example, in U.S. Pat. No. 3,117,126 and British Pat. Nos. 932,644, 957,570 and 959,054.

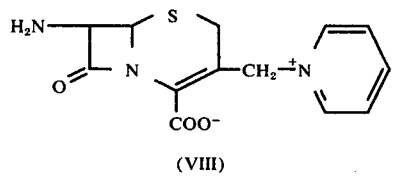

(VIII)

The 3-thiolated 7-aminocephalosporanic acids can be obtained by reacting 7-aminocephalosporanic acid with the appropriate thiol as described in U.S. Pat. No. 3,516,997. Thus when 5-methyl-1,3,4-thiadiazole-2-thiol is employed the compound 7-amino-3-[(5-methyl-1,3,4-thiadiazol-2-ylthio)methyl]decephalosporanic acid is obtained, which has the formula

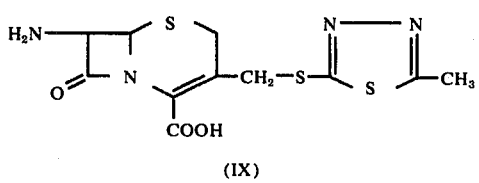

(IX)

When the compound 1-methyl-1,2,3,4-tetrazole-5-thiol is employed the compound 7-amino-3-[(1-methyl-1,2,3,4-tetrazol-5-ylthio)methyl]decephalosporanic acid is obtained having the formula

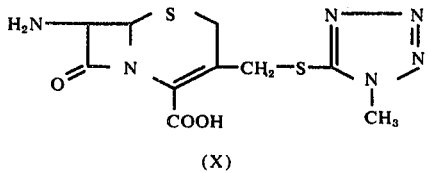

(X)

The 2,4-dioxo-1-pyrimidinyl carboxylic acids (II) used as starting materials are for the most part known compounds which are synthesized in one or two steps via the condensation of an alkali metal salt of a 2,4-dioxo-pyrimidine (XI) with ethylbromoacetate or a substituted ethylbromoacetate (XII). The potassium salt of 2,4-dihydroxy-pyrimidine is generally preferred to effect condensation, and the resulting ester hydrolyzed to the 2,4-dioxo-1-pyrimidinyl-(substituted)-acetic dinyl-(substituted)-acetic acid (II) with an aqueous base as illustrated in the following reaction scheme:

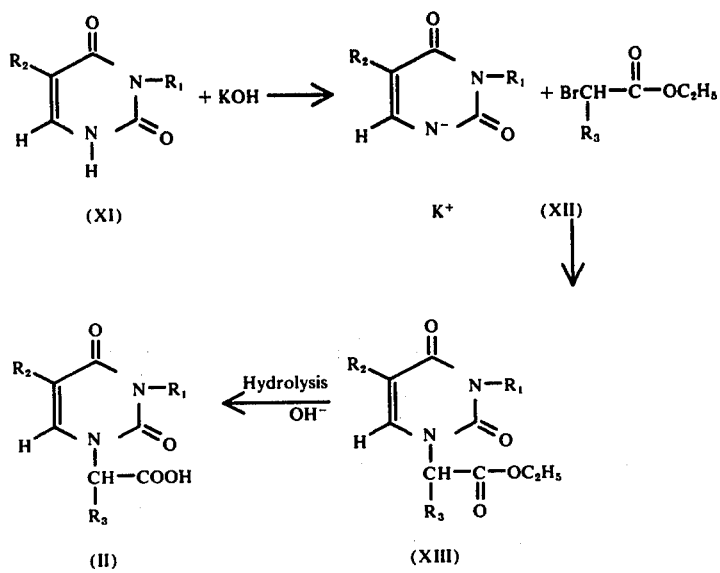

Alternatively, the 2,4-dioxo-1-pyrimidinyl-(substituted)-acetic acids (II) are directly prepared by the reaction of a 2,4-pyrimidinedione with chloroacetic acid or a substituted chloroacetic acid (XIV) in the presence of a strong aqueous base as indicated in the following reaction scheme:

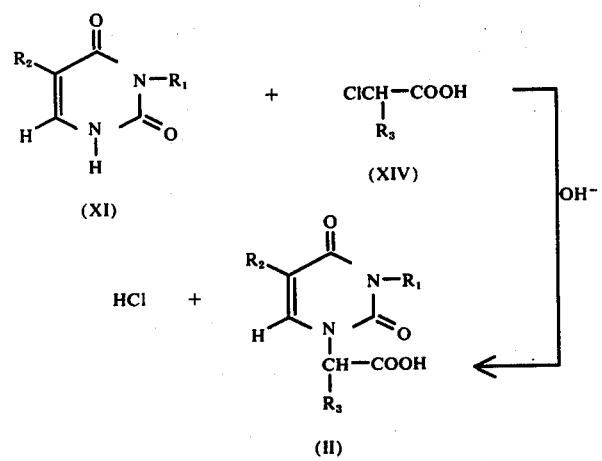

The 2,4-dioxo-1-pyrimidinyl-(substituted)-acetic acid derivatives (II) in which the 5-position is substituted with an acetyl, cyano, carbomethoxy or carbethoxy group, can also be prepared by the reaction of a suitable amino acid (XVII) with a substituted ethoxyacrylamide derivative (XVI). The substituted ethoxyacrylamide derivatives in turn, are prepared by the condensation of a substituted N-acetoacetylurethane (XIV) with triethyl orthoformate (XV) in refluxing acetic anhydride. This series of reactions can be illustrated by the following reaction scheme

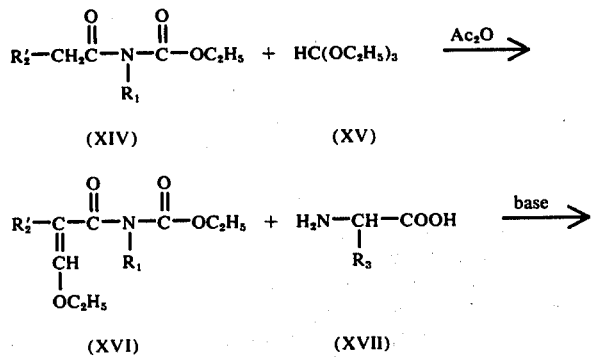

-continued

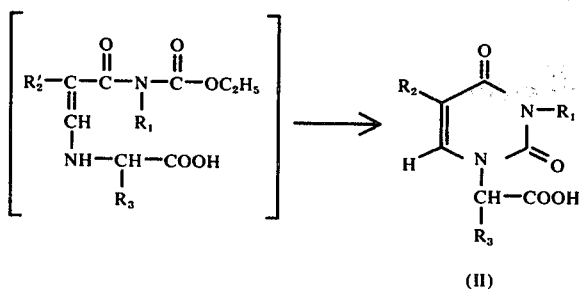

(II)

wherein $R_2'$ represents acetyl, cyano, carbomethoxy and carbethoxy, a subgroup of the group represented by $R_2$, and $R_1$ and $R_3$ have the values previously assigned.

The substituted N-acetoacetylurethane (XIV) used as a starting material in the above reaction sequence, when substituted with an acetyl radical, can be prepared according to the procedure of Dewar and Shaw, J. Chem. Soc., 3254 (1961). When substituted with a cyano radical the starting material can be prepared as described by Atkinson, Shaw and Warrener, J. Chem. Soc., 4118 (1956). The carbomethoxy and carbethoxy derivatives of XIV are prepared in accordance with the procedure of Holy, Collect. Czech. Chem. Commun, 37, 1555 (1972).

The 6-aminopenicillanic acid or a 7-aminocephalosporanic acid (III) can be directly coupled with a 2,4-dioxo-1-pyrimidinyl-(substituted)-acetic acid (II). Alternatively, the β-lactam acid may be coupled as its neutral salt (preferably as the sodium or triethylamine salt) or coupled as its β-lactam ester. Esters represented by Formula (III) are those in which the free carboxyl group of the β-lactam compound has been esterified. Since the ester group is to be removed following the coupling reaction, preference is given to those ester groups which can be readily removed to regenerate the free carboxylic acid, as for example, by solvolysis, hydrogenolysis or via a nucleophilic exchange, without affecting or changing the remaining portion of the molecule. Esterification groups that are readily converted to the free carboxylic acid under mild conditions are the silylated and stannylated carboxyl groups. These groups are formed by treating compounds having a free carboxyl group with a suitable silylating agent, as for example, an alkyl disilazane such as hexamethyldisilazane. Suitable stannylating agents include, for example, a bis-(tri-lower alkyl-tin-)oxide such as bis-(tri-n-butyl tin)-oxide; a tri-lower alkyl tin-hydroxide such as triethyl tin hydroxide; a tri-lower alkoxy-tin compound such as triethoxy tin hydroxide; and a tri-lower alkyl-tin halide such as tri-n-butyl-tin chloride. The resulting silylated or stannylated carboxyl group can be regenerated to the desired free carboxylic acid by treatment with a neutral, hydrogen-donating agent. Water or a lower alkanol, as for example, ethanol, is preferably used as the hydrogen-donating agent.

With regard to the 2,4-dioxo-1-pyrimidinyl-(substituted)-acetic acids (II) which are used to couple with the 6-aminopenicillanic or 7-aminocephalosporanic acids, functional equivalents other than the free (substituted)-acetic acid may also be employed. Examples of such reactive equivalents include the corresponding acid halides, acid azides, mixed acid anhydrides with alkylphosphoric acid or alkyl-carbonic acid, acid amides with imidazole or a 4-substituted imidazole, acid cyanomethyl esters and acid p-nitrophenyl esters.

Preferably the coupling reaction is conducted in the presence of a condensing agent such as dicyclohexylcarbodimide, N-cyclohexyl-N'-morpholinoethylcarbodiimide, pentamethyleneketone-N-cyclohexylimine, N-ethyl-phenylisoxazolium-3'-sulfonate, and phosphorous trichloride. Under such circumstances the reaction is believed to proceed through an active form of the carboxyl radical in the 2,4-dioxo-1-pyrimidinyl-(substituted)-acetic acid or via the amino radical of the 6-aminopenicillanic acid or the 7-aminocephalosporanic acid.

The coupling reaction is generally conducted in the presence of a suitable solvent. Suitable solvents include acetone, dioxane, acetonitrile, chloroform, ethylene chloride, tetrahydrofuran or other inert, commonly used solvents. The reaction can be further carried out in the presence of a base such as an alkali metal carbonate, trialkylamine or pyridine. Generally the reaction is conducted at room temperature or below.

Upon completion of the coupling reaction, generally after a period ranging from 30 minutes to 4 hours, the reaction product is isolated using conventional methods well known to those skilled in the art.

The novel compounds of the present invention are biologically active and have been found to possess good antibacterial activity. Thus, they are useful antimicrobial agents having a broad-spectrum in vitro antimicrobial activity against standard laboratory microorganisms which are used to screen for activity against pathogenic bacteria. The antibacterial spectrum of typical compounds of the present invention is determined in a standard manner by the agar-dilution streakplate technique commonly used in the testing of new antibiotics. The high in vitro antibacterial activity of the novel compounds of this invention not only makes them useful as pharmacological agents per se, but makes them useful as additives for animal feeds, as well as additives for materials which are subject to microbial deterioration, such as cutting oils and fuel oils. These compounds are also useful for their antibacterial effect in soaps, shampoos and in topical compositions for the treatment of wounds and burns.

The invention described herein is more particularly illustrated in conjunction with the following specific examples.

EXAMPLE 1

2-(2,4-Dioxo-1-pyrimidinyl)acetic acid

A solution of 2,4-dioxo-pyrimidine (22 g, 0.2 mole) in a 1 N solution of potassium hydroxide is heated to its reflux temperature and chloroacetic acid (18 g, 0.2 mole) is added portionwise. After 18 hours at reflux temperature, the reaction mixture is chilled, acidified and filtered to yield 20 g of white 2,4-dioxo-1-pyrimidinylacetic acid having a m.p. of 285° C.

EXAMPLE 2

2-(5-Cyano-2,4-dioxo-1-pyrimidinyl)acetic acid

The compound α-cyano-β-ethoxy-N-ethoxycarbonylacrylamide (21.2 g, 0.1 mole), prepared in accordance with the procedure of M. R. Atkinson, G. Shaw and R. N. Warrener, J. Chem. Soc., 4118 (1956), is added in portions to a solution of glycine (7.5 g, 0.1 mole) dissolved in 2 Normal sodium hydroxide (50 ml). After solution is achieved, 8 ml of a 50% sodium hydroxide solution is added, the mixture is stirred for a period of 18 hours, chilled, acidified and filtered to give 6 g of 5-cyano-2,4-dioxo-1-pyrimidinylacetic acid having a m.p. of 265° C.

EXAMPLE 3

2-(5-Acetyl-2,4-dioxo-1-pyrimidinyl)-2-phenylacetic acid

The compound α-acetyl-β-ethoxy-N-ethoxycarbonylacrylamide (11.4 g, 0.05 mole), prepared according to J. H. Dewar and G. Shaw, J. Chem. Soc., 3254 (1961), is added to a solution of α-phenylglycine (7.6 g, 0.05 mole) in 2 N sodium hydroxide (50 ml). The reaction mixture is heated on a steam bath for 5 minutes, chilled, acidified and filtered to yield 4 g of 2-(5-acetyl-2,4-dioxo-1-pyrimidinyl)phenylacetic acid having a m.p. of 221°–3° C. (dec.)

EXAMPLE 4

7-[2-(2,4-Dioxo-1-pyrimidinyl)acetylamino]-cephalosporanic acid, sodium salt

The compound 2,4-dioxo-1-pyrimidinylacetic acid (3.4 g, 0.02 mole) is dissolved in dimethylformamide (50 ml) and the solution is chilled to 0° C. Carbonylidiimidazole (3.2 g, 0.02 mole) is added and the mixture is stirred under nitrogen at 0° C. for 30 minutes and then warmed to room temperature. The reaction flask is evacuated for 30 minutes and chilled to −20° C. In a separate flask, 7-aminocephalosporanic acid is silylated by heating a suspension of 7-aminocephalosporanic acid (5.4 g, 0.02 mole) with hexamethyldisilazane (8 ml) in chloroform (50 ml) at reflux temperature for 30 minutes. This solution is evaporated to dryness to remove the liberated ammonia. A solution of the residue is chloroform (50 ml) is chilled to −20° C. and added to the imidazolide. The reaction mixture is stirred at 0° C. for 1 hour, warmed to room temperature and stirred overnight.

The solution is treated with 2 ml of methanol and the precipitated 7-aminocephalosporanic acid is removed by filtration. A solution of sodium 2-ethylhexanoate in n-butanol (10 ml of a 2 N solution) is added, and the mixture is diluted with ether to an approximate volume of 1 liter in order to precipitate the product. After reprecipitation from methanol with ether, a yield of 2.0 g of white 7-[2-(2,4-dioxo-1-pyrimidinyl)acetylamino]-cephalosporanic acid, m.p. 240° C. (dec.) is obtained. Iodine titration indicated a purity of 98.5%.

Repeat essentially the same procedure but substituting 7-amino-desacetylcephalosporanic acid, 7-amino-3-[(1-methyl-1,2,3,4-tetrazole-5-ylthio)methyl]-decephalosporanic acid and 7-amino-3-[(5-methyl-1,3,4-thiazole-2-ylthio)methyl]cephalsporanic acid for 7-aminocephalosporanic acid results in the preparation of the sodium salts of 7-[2-(2,4-dioxo-1-pyrimidinyl)acetylamino]desacetlycephalosporanic acid, 7-[2-(2,4-dioxo-1-pyrimidinyl)-acetylamino]-3-(1-methyl-1,2,3,4-tetrazole-5-ylthio)-methyl]decephalosporanic acid and 7-[2-(2,4-dioxo-1-pyrimidinyl)acetylamino]-3-[(5-methyl-1,3,4-thiadiazole-2-ylthio)methyl]cephalosporanic acid, respectively.

EXAMPLE 5

7-[2-(5-Cyano-2,4-dioxo-1-pyrimidinyl)acetylamino]-cephalosporanic acid, sodium salt The compound (5-cyano-2,4-dioxo-1-pyrimidinyl)acetic acid (3.9 g, 0.02 mole) is dissolved in dimethylformamide (50 ml) and the solution is chilled to 0° C. Carbonyldimidazole (3.2 g, 0.02 mole) is added and the mixture is stirred under nitrogen at 0° C. for 30 minutes and then warmed to room temperature. The reaction flask is evacuated for 30 minutes and chilled to −20° C. In a separate flask, 7-aminocephalosporanic acid is silylated by heating a suspension of 7-aminocephalosporanic acid (5.4 g, 0.02 mole) and hexamethyldisilazane (8 ml) in chloroform (50 ml) at reflux for 30 minutes. This solution is evaporated to dryness to remove the liberated ammonia. A solution of the residue in chloroform (50 ml) is chilled to −20° C. and added to the imidazolide. The reaction mixture is stirred at 0° C. for 1 hour, warmed to room temperature and stirred overnight.

The solution is treated with 2 ml of methanol and the precipitated 7-aminocephalosporanic acid is removed by filtration. A solution of sodium 2-ethylhexanoate in n-butanol (10 ml of a 2 N solution) is added, and the mixture is diluted with ether to an approximate volume of 1 liter in order to precipitate the product.

The solid is dissolved in water (100 ml) and the solution is layered with ethyl acetate (100 ml). The solution is vigorously stirred and acidified (pH 2) with a 6 N hydrochloric acid solution. The mixture is filtered and the organic layer is separated from the filtrate. The aqueous layer is extracted with another 100 ml of ethyl acetate. The combined ethyl acetate layers are dried (magnesium sulfate) and a sodium 2-ethylhexanoate solution (10 ml of a 2 N solution in n-butanol) is added.

The resulting precipitate is filtered off and vacuum dried to yield 0.7 g of 7-[2-(5-cyano-2,4-dioxo-1-pyrimidinyl) acetylamino]cephalosporanic acid having a m.p. of 272° C. (dec.)

Following essentially the same procedure but substituting 2-(2,4-dioxo-5-nitro-1-pyrimidinyl)acetic acid, 2-(2,4-dioxo-5-methyl-1-pyrimidinyl)phenylacetic acid, 2-(5-bromo-2,4-dioxo-1-pyrimidinyl)acetic acid, 2-(5-carbethoxy-2,4-dioxo-1-pyrimidinyl)-2-methylacetic acid and 2-(2,4-dioxo-3-methyl-1-pyrimidinyl)acetic acid for the 2-(5-cyano-2,4-dioxo-1-pyrimidinyl)acetic acid above, results in the preparation of the sodium salts of 7-[2-(2,4-dioxo-5-nitro-1-pyrimidinyl)acetylamino]cephalosporanic acid, 7-[2-(2,4-dioxo-5-methyl-1-pyrimidinyl)-2-phenylacetylamino]cephalosporanic acid, 7-[2-(5-bromo-2,4-dioxo-1-pyrimidinyl)acetylamino]cephalosporanic acid, 7-[2-(5-carbethoxy-2,4-dioxo-1-pyrimidinyl-2-methylacetylamino]cephalosporanic acid, 7-[2-(2,4-dioxo-3-methyl-1-pyrmidinyl)acetylamino]cephalosporanic acid, respectively.

EXAMPLE 6

6-[2-(5-Acetyl-2,4-dioxo-1-pyrimidinyl)-acetylamino]-penicillanic acid, sodium salt A solution of 2-(5-acetyl-2,4-dioxo-1-pyrimidinyl)-acetic acid (1.9 g, 0.0082 mole) in dimethylformamide (25 ml) is chilled to −5° C. and carbonyldiimidazole (1.3 g, 0.0082 mole) is added in one portion. The mixture is stirred at −5° to 0° C. under an atmosphere of nitrogen for 1 hour and evacuated for 15 minutes to remove the carbon dioxide evolved in the imidazolide formation.

At −10° C. a solution of 6-aminopenicillanic acid (1.75 g, 0.0082 mole) and triethylamine (2 g, 0.02 mole) in chloroform (25 ml) is added. The reaction mixture is stirred at −10° C. for 1 hour, warmed to room temperature and 5 ml of a 2 N solution of sodium 2-ethylhexanoate in n-butanol is added. Precipitation of the product is completed by the addition of ether (500 ml). The solid is isolated by filtration and vacuum dried to give 2.7 g of white solid which is a mixture of 6-aminopenicillanic acid and the product.

The solid mixture is dissolved in 70 ml of cold water and the resulting solution is layered with ethyl acetate (70 ml). While the mixture is being stirred, a solution of 6 N HCl is added to adjust the acidity to a pH of 2. The layers are separated and the aqueous layer is extracted with another 70 ml of ethyl acetate. The combined ethyl acetate extracts are dried (magnesium sulfate) and filtered. The filtrate is treated with 5 ml of the sodium 2-ethylhexanoate solution and the ethyl acetate is decanted from the precipitate. After reprecipitation from methanol with ether one obtains 1.2 g of white solid, m.p. 227° C. (dec.)

Following essentially the same procedure but substituting 2-(2,4-dioxo-1-pyrimidinyl)acetic acid, 2-(2,4-dioxo-5-methyl-1-pyrimidinyl)acetic acid, 2-(5-cyano-2,4-dioxo-1-pyrimidinyl)acetic acid, 2-(2,4-dioxo-5-methyl-1-pyrimidinyl)-2-methylacetic acid, 2-(5-acetyl-2,4-dioxo-1-pyrimidinyl)-2-phenylacetic acid, and 2-(2,4-dioxo-3-methyl-1-pyrimidinyl)acetic acid for the 2-(5-acetyl-2,4-dioxo-1-pyrimidinyl)acetic acid above, results in the formation of the sodium salts of 6-[2-(2,4-dioxo-1-pyrimidinyl)acetylamino]penicillanic acid, 6-[2-(2,4-dioxo-5-methyl-1-pyrimidinyl)acetylamino]penicillanic acid, 6-[2-(5-cyano-2,4-dioxo-1-pyrimidinyl)acetylamino]penicillanic acid, 6-[2-(2,4-dioxo-5-methyl-1-pyrimidinyl)-2-methylacetylamino]-penicillanic acid, 6-[2-(5-acetyl-2,4-dioxo-1-pyrimidinyl)-2-phenylacetylamino]-penicillanic acid, and 6-[2-(2,4-dioxo-3-methyl-1-pyrimidinyl)acetylamino]penicillanic acid, respectively.

EXAMPLE 7

7-[2-(2,4-Dioxo-1-pyrimidinyl)acetylamino]-3-pyridinium decephalosporanic acid A solution of 7-[2-(2,4-dioxo-1-pyrimidinyl)acetylamino]cephalosporanic acid, sodium salt (4.8 g, 0.01 mole), potassium thiocyanate (0.02 mole) and pyridine (0.03 mole) in water (15 ml) is treated with 85% phosphoric acid to obtain a pH of 6.5. The reaction mixture is heated at 60° C. for 6 hours and the 7-[2-(2,4-dioxo-1-pyrimidinyl)acetylamino]-3-pyridinium decephalosporanic acid is isolated according to the procedure described by J. L. Spencer, et. al., J. Org. Chem., 32, 500 (1967).

EXAMPLE 8

7-[2-(2,4-Dioxo-1-pyrimidinyl)acetylamino]desacetyl-cephalosporanic acid

A solution of 7-[2-(2,4-dioxo-1-pyrimidinyl)acetylamino]cephalosporanic acid, sodium salt in water is treated with an acetyl esterase isolated from orange peel following the procedure of J. D'A. Jeffery, Biochem. J. 81, 591 (1961). The compound, 7-[2(2,4-dioxo-1-pyrimidinyl)-acetylamino]desacetylcephalosporanic acid which is obtained is isolated following essentially the same procedure described therein.

EXAMPLE 9

Specific nutrient agar plates are completely innoculated with various test organisms. Filter paper discs are placed on the surface of the agar and wetted with 0.1 ml of a solution containing 10, 100 and 1,000 micrograms of the test compound. Zones of inhibition of microbial growth are used to indicate the antibacterial activity of the test compound against the various test organisms employed.

The following table summarizes the in vitro activity of the following representative compounds: 6-[2-(2,4-dioxo-1-pyrimidinyl)acetylamino]penicillanic acid (1), 6-[2-(2,4-dioxo-5-methyl-1-pyrimidinyl)acetylamino]-penicillanic acid (2), 7-[2-(2,4-dioxo-1-pyrimidinyl)acetylamino]desacetoxycephalosporanic acid (3), 7-[2-(2,4dioxo-5-methyl-1-pyrimidinyl)acetylamino]-desacetoxycephalosporanic acid (4), 6-[2-(5-acetyl-2,4-dioxo-1-pyrimidinyl)acetylamino]penicillanic acid (5), 6-[2-(5-cyano-2,4-dioxo-1-pyrimidinyl)acetylamino]penicillanic acid (6) 6-[2-(2,4-dioxo-5-methyl-1-pyrimidinyl)-2-methylacetylamino]penicillanic acid (7), 6-[2-(5-acetyl-2,4-dioxo-1-pyrimidinyl)2-phenylacetylamino]penicillanic acid (8), and 7-[2(2,4-dioxo-1-pyrimidinyl)acetylamino]-cephalosporanic acid (9).

| | MINIMAL INHIBITING CONCENTRATION (mcg/ml) | | | | |
|---|---|---|---|---|---|
| Compound | Staphylococcus aureus | Salmonella schottmuelleri | Streptococcus pyogenes | (Penicillinase Producing) Staphylococcus aureus | Acid Resistance |
| (1) | 10 | 1,000 | 10 | 1,000 | Yes |
| (2) | 10 | 100 | 10 | >1,000 | Yes |
| (3) | >1,000 | >1,000 | 1,000 | 1,000 | |
| (4) | 1,000 | >1,000 | 1,000 | 1,000 | Yes |
| (5) | 10 | 1,000 | >1,000 | 1,000 | Yes |
| (6) | 10 | 100 | 1,000 | 1,000 | Yes |
| (7) | 10 | 1,000 | 100 | 1,000 | Yes |
| (8) | 10 | 1,000 | 1,000 | 1,000 | Yes |

| Compound | Staphylococcus aureus | Salmonella schottmuelleri | Streptococcus pyogenes | (Penicillinase Producing) Staphylococcus aureus | Acid Resistance |
|---|---|---|---|---|---|
| (9) | 10 | 100 | 100 | 1,000 | Yes |

We claim:

1. A 6-[(2,4-dioxo-1-pyrimidinyl)acylamino]penicillin derivative having the formula:

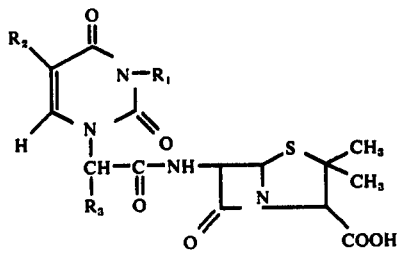

wherein $R_1$ is hydrogen and methyl;

$R_2$ is selected from the group consisting of hydrogen, halogen, hydroxyl, lower alkyl, trifluoromethyl, nitro, amino, acetyl, cyano, carboxy, carbomethoxy and carbethoxy;

$R_3$ is selected from the group consisting of hydrogen, methyl, phenyl, carboxy, carbomethoxy and carbethoxy; and the pharmaceutically acceptable salts thereof.

2. A compound according to claim 1 wherein $R_1$ is hydrogen.

3. A compound according to claim 1 wherein $R_3$ is hydrogen.

4. A compound of claim 1 which is 6-[2-(5-cyano-2,4-dioxo-1-pyrimidinyl)acetylamino]penicillanic acid.

* * * * *